United States Patent
Pitalo

(10) Patent No.: US 12,171,683 B2
(45) Date of Patent: Dec. 24, 2024

(54) MODULAR MULTI-POSITIONAL RIGID SPLINTING DEVICE

(71) Applicant: Christian Matthew Pitalo, Ocean Springs, MS (US)

(72) Inventor: Christian Matthew Pitalo, Ocean Springs, MS (US)

(*) Notice: Subject to any disclaimer, the term of this patent is extended or adjusted under 35 U.S.C. 154(b) by 271 days.

(21) Appl. No.: 17/088,957

(22) Filed: Nov. 4, 2020

(65) Prior Publication Data

US 2021/0346187 A1    Nov. 11, 2021

Related U.S. Application Data

(60) Provisional application No. 63/022,452, filed on May 9, 2020.

(51) Int. Cl.
*A61F 5/01* (2006.01)
*A61F 5/058* (2006.01)

(52) U.S. Cl.
CPC .......... *A61F 5/0125* (2013.01); *A61F 5/013* (2013.01); *A61F 5/058* (2013.01);
(Continued)

(58) Field of Classification Search
CPC ...... A61F 5/058; A61F 5/0118; A61F 5/0125; A61F 5/373; A61F 5/013; A61F 5/05866; A61F 13/107; A61F 2005/0141; A61F 5/0102; A61F 5/05858; A61F 5/042; A61F 2005/0158; A61F 2005/0167; A61F 2005/018; A61F 2005/016; A61F 5/0123; A61F 2005/0137; A61F 5/0193; A61F 2005/0134; A61F 5/0106; A61F 5/05825;
(Continued)

(56) References Cited

U.S. PATENT DOCUMENTS 2,702,542 A * 2/1955 Gessel ............... A61F 5/0193
602/24
3,439,672 A * 4/1969 Fisher ................ A61F 5/058
403/324

(Continued)

OTHER PUBLICATIONS

Li Zemei, "A kind of adjustable joint protection brace with self-locking function", CN-109259921-A, Assignee: Xiamen Jess Medical Instruments Co Ltd, Nov. 29, 2018, Machine Translated (Year: 2018).*

(Continued)

*Primary Examiner* — Keri J Nelson
(74) *Attorney, Agent, or Firm* — Intellectual Property Consulting, LLC; Stephen Kepper

(57) ABSTRACT

The present invention describes a multi-positional, modular bodily limb splinting system consisting of at least one pair of rigid, shared geometry interlocking male and female splint members which allow for expedient placement and treatment of a limb injury. The male splint member includes a locking post and an adjustable locking post at one end, and the female splint member includes a locking aperture operable to receive and interlock with the locking post and a plurality of adjustable apertures operable to receive and interlock with the adjustable locking post. The male and female splint members of various lengths may be positioned into one or more of several incremental angled configurations of up to 360° to conform to the extremity injury.

19 Claims, 7 Drawing Sheets

(52) U.S. Cl.
CPC ...... *A61F 5/05825* (2013.01); *A61F 5/05841* (2013.01); *A61F 2005/0141* (2013.01); *A61F 2005/0158* (2013.01); *A61F 2005/0165* (2013.01); *A61F 2005/0167* (2013.01)

(58) Field of Classification Search
CPC ...... A61F 5/05841; A61F 5/0585; A61F 5/37; A61F 2005/0165; A61F 5/0104; A61F 5/0116; A61F 5/04; A61F 5/05; A41D 19/01582; A61H 1/0277; A61H 1/0237; A61H 1/0274; A61H 1/024; A61H 2201/1261; Y10T 403/32426; Y10T 403/32451; Y10T 403/32327; Y10T 403/32221; Y10T 403/32262; Y10T 403/32336; Y10T 403/32368; Y10T 403/32361

See application file for complete search history.

(56) References Cited

U.S. PATENT DOCUMENTS

| | | | | |
|---|---|---|---|---|
| 5,358,471 | A * | 10/1994 | Klotz | A61F 5/05866 602/5 |
| 5,409,449 | A * | 4/1995 | Nebolon | A61F 5/0125 602/76 |
| 5,506,040 | A * | 4/1996 | Cordani | B32B 5/26 428/218 |
| 7,364,557 | B2 * | 4/2008 | Yumikino | A61F 5/0125 602/19 |
| 8,603,018 | B2 * | 12/2013 | Anglada | A61F 5/013 473/213 |
| 10,617,549 | B2 * | 4/2020 | Frost | A61F 5/05 |
| 11,234,854 | B2 * | 2/2022 | Kosiorek | A61F 5/05825 |
| 11,241,326 | B2 * | 2/2022 | Wagner | A61F 5/0102 |
| 2017/0281389 | A1 * | 10/2017 | Frost | A61F 5/0125 |
| 2018/0042748 | A1 * | 2/2018 | Wagner | A61F 5/058 |

OTHER PUBLICATIONS

Erich Albrecht, Hans-Georg Opahle "Orthesis having distal and proximal rails, linkage, spring arrangement, traction or thrust element, link point and force transmission element", DE-19904554-A1, Assignee: Albrecht GmbH, Feb. 4, 1999, Machine Translated (Year: 1999).*

Hans Grundei, "Guide rail for a knee joint orthosis with one joint" DE-3825813-C2, Assignee: Schuett & Grundei Orthopaedietechnik GMBH, 2400 LU, Jul. 29, 1988, Machine Translated (Year: 1988).*

* cited by examiner

MODULAR MULTI-POSITIONAL RIGID SPLINTING DEVICE

RELATED APPLICATIONS

This application claims priority to U.S. Provisional Application No. 63/022,452 filed May 9, 2020. The entire contents of the above application are hereby incorporated by reference as though fully set forth herein.

FIELD

The present invention relates to devices used as splints. More particularly, the invention relates to a modular multi-positional rigid splinting device for use in both pre-clinical and clinical settings.

BACKGROUND

The need for an easily transported, rigid, reusable and mechanically simplistic splinting system exists both inside and outside of the medical community, especially in physical activities where the risk of extremity injury is present such as in hiking or other sports. Preferred embodiments of the invention allow for stabilization of an extremity injury, especially in a pre-clinical or emergency setting, to occur expeditiously with minimal assembly, resulting in a savings of time and effort for the user and/or patient. The invention can also be adjusted to accommodate the swelling of the extremity and/or affected joint. The shape and construction of the splint halves provide both consistent rigidity and stability not easily obtained by existing systems.

Certain existing splinting and stability systems have been previously developed for treatment of pre-clinical/field extremity injuries. These systems, though quickly deployable and easily transported, suffer drawbacks such as a lack of permanent rigidity necessary to maintain the stabilization of an injured extremity under compression conditions such as that of an impact or applied weight. These existing systems are prone to deformation with repeated use which could increase the likelihood of further patient injury.

BRIEF SUMMARY OF THE INVENTION

The present invention describes a multi-positional, modular bodily limb splinting system consisting of at least one pair of rigid, shared geometry interlocking segments which allow for expedient placement and treatment of a limb injury.

In one embodiment the invention includes a male splint member with a locking post and an adjustable locking post at one end and a female splint member a locking aperture operable to receive and interlock with the locking post and a plurality of adjustable apertures operable to receive and interlock with the adjustable locking post. The interlocking mechanism of the embodiment allows the alignment of the male splint member and the female splint member to be angularly adjusted in a multitude of positions as indicated by the patient's injury. The configured splint is held to the extremity by fastening means, including the use of binding straps. The interlocking male and female splint members are configured to be stacked upon themselves and secured for storage and/or transport using the elements' shared geometrical design features. The singular components require no additional construction beyond the joining of the splint members and the strapping of them to the extremity.

The configured splint may be applied to any extremity in any position or direction, including (but not limited to) anterior, posterior, lateral, and medial positions of an extremity for the purposes of stabilization. The system provides static components for precise positioning of the injured joint or extremity, which in turn allows adjustment and repositioning to be executed quickly.

BRIEF DESCRIPTION OF THE DRAWINGS

The foregoing and other objects, features, and advantages of the invention are apparent from the following detailed description taken in conjunction with the accompanying drawings in which like parts are given like reference numerals and, wherein.

Figure 1:
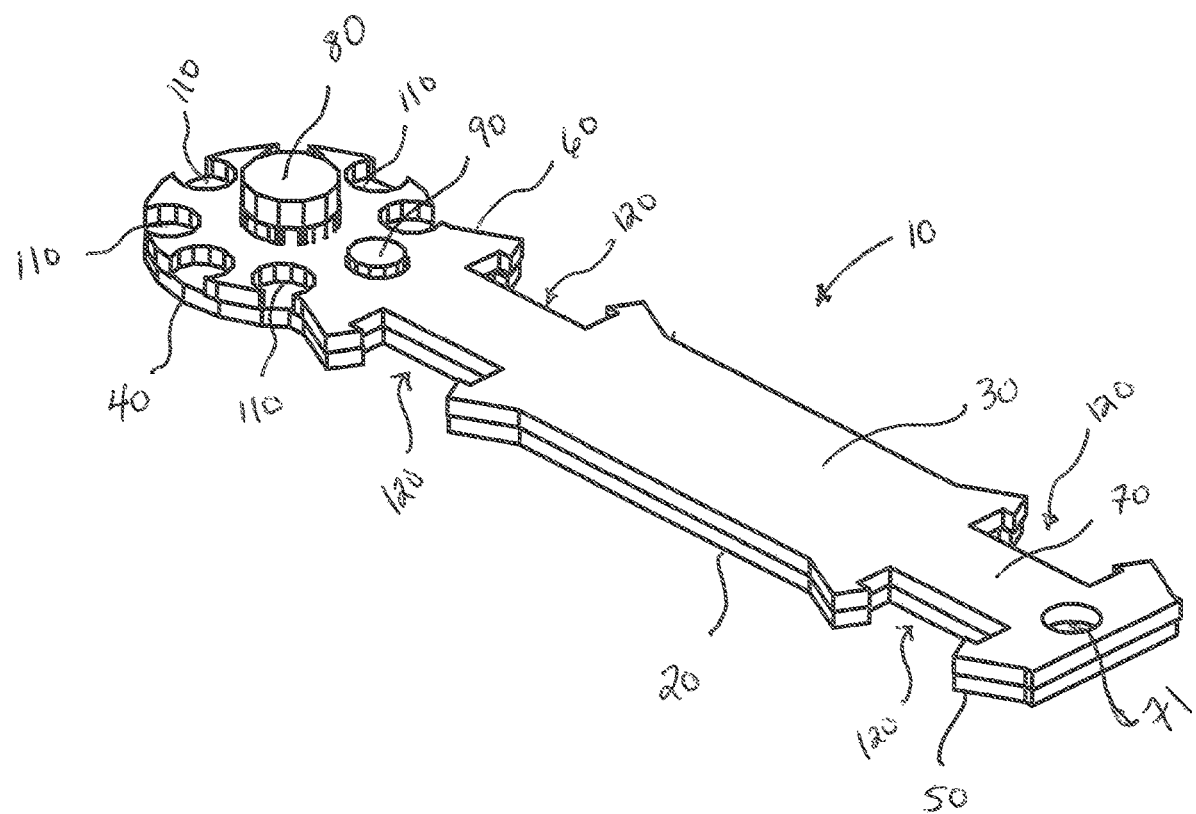
FIG. 1 depicts a perspective view of the splint halves joined in a stacked configuration according to various embodiments herein.

The images in the drawings are simplified for illustrative purposes and are not depicted to scale. Within the descriptions of the figures, similar elements are provided similar names and reference numerals as those of the previous figure(s). The specific numerals assigned to the elements are provided solely to aid in the description and are not meant to imply any limitations (structural or functional) on the invention.

The appended drawings illustrate exemplary configurations of the invention and, as such, should not be considered as limiting the scope of the invention that may admit to other equally effective configurations. It is contemplated that features of one configuration may be beneficially incorporated in other configurations without further recitation.

DETAILED DESCRIPTION

For a further understanding of the nature and function of the embodiments, reference should be made to the following detailed description. Detailed descriptions of the embodiments are provided herein, as well as, the best mode of carrying out and employing the present invention. It will be readily appreciated that the embodiments are well adapted to carry out and obtain the ends and features mentioned as well as those inherent herein. It is to be understood, however, that the present invention may be embodied in various forms. Therefore, persons of ordinary skill in the art will realize that the following disclosure is illustrative only and not in any way limiting, as the specific details disclosed herein provide a basis for the claims and a representative basis for teaching to employ the present invention in virtually any appropriately detailed system, structure or manner. It should be understood that the devices, materials, methods, procedures, and techniques described herein are presently representative of various embodiments. Other embodiments of the disclosure will readily suggest themselves to such skilled persons having the benefit of this disclosure.

Turning to FIG. 1, the splint 10 having a male splint member 20 and a female splint member 30 is shown in a stacked configuration with the male splint member 20 positioned beneath the female splint member 30.

Figure 8:
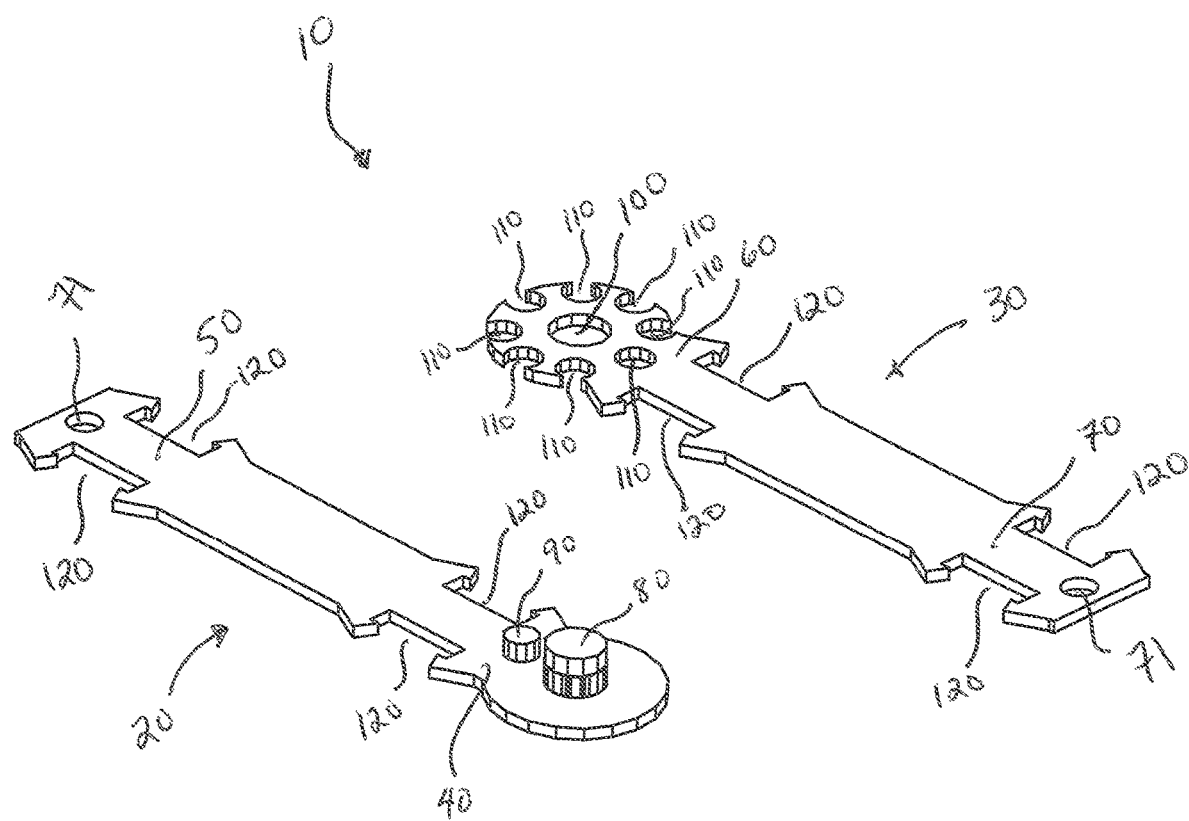
FIG. 8 depicts a perspective view of the splint halves separated from one another according to various embodiments herein.

As shown more clearly in FIG. 8, the male splint member 20 includes a first end 40 and an opposing second end 50. The first end 40 can come in a variety of shapes and sizes, but at a minimum, must include a locking post 80, preferably positioned in the radial center of the first end 40 and an adjustable locking post 90 offset from the locking post 80. The female member 30 has a first end 60 opposite a second end 70. Like its male counterpart, the first end 60 can come in a variety of shapes and sizes, but the preferred embodiment includes a locking aperture 100 positioned, preferably positioned at its radial center that is operable to receive the locking post 80 of the male splint member 20, and a plurality of adjustable locking apertures 110 disposed circumferentially along the perimeter of the first end 60, each operable to receive the adjustable locking post 90.

Figure 9:
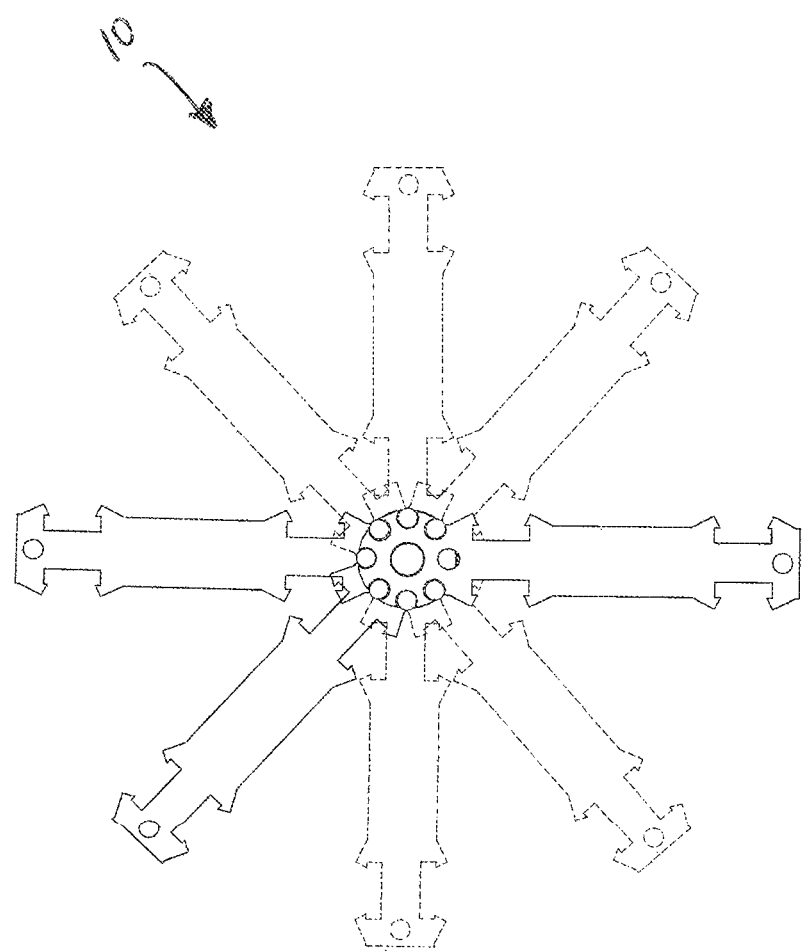
FIG. 9 depicts a top-down view of the splint halves interlocked in potential positioning combinations according to various embodiments herein.

The male splint member 20 and female splint member 30 are locked in a fixed position when first end 60 of the female splint member 30 is placed over the first end 40 of the male splint member 20 such that the locking post 80 is slotted through the locking aperture 100 and the adjustable locking post 90 is slotted through one of the plurality of adjustable locking apertures 110 (as shown in FIGS. 1-4 and 9-11). This means for interlocking the male splint member 20 and female splint member 30 allow the splint 10 to be assembled ambidextrously in any direction or angle from 0 to 360°. In FIG. 9, the dashed lines more clearly depict potential positioning for the interlocked male and female splint members 20, 30 at incremental angles within a 360° range.

In preferred embodiments, the male splint member 20 and female splint member 30 may be made from a variety of thermoplastic or metallic materials, including but not limited to, Acrylonitrile butadiene styrene and polylactic acid thermoplastics, in addition to aluminum or similar metals, or suitable materials which may produce a suitably durable and rigid surface.

Turning back to FIG. 1, the male splint member 20 and female splint member 30 interlock such that the members 20, 30 are stacked upon each other, which allow for increased rigidity if being used for splinting a bodily limb, or alternatively, allow for easier transport and storage of the splint 10 when not in use. The second end 50 of the male splint member 20 and the second 70 of the female splint member may also include a mounting aperture 71 operable to receive a mounting accessory (e.g. a carabiner) that, when stacked as shown in FIG. 1, allow for the members 20,30 to be mounted to another accessory (e.g. belt) using the mounting accessory.

Figure 10:
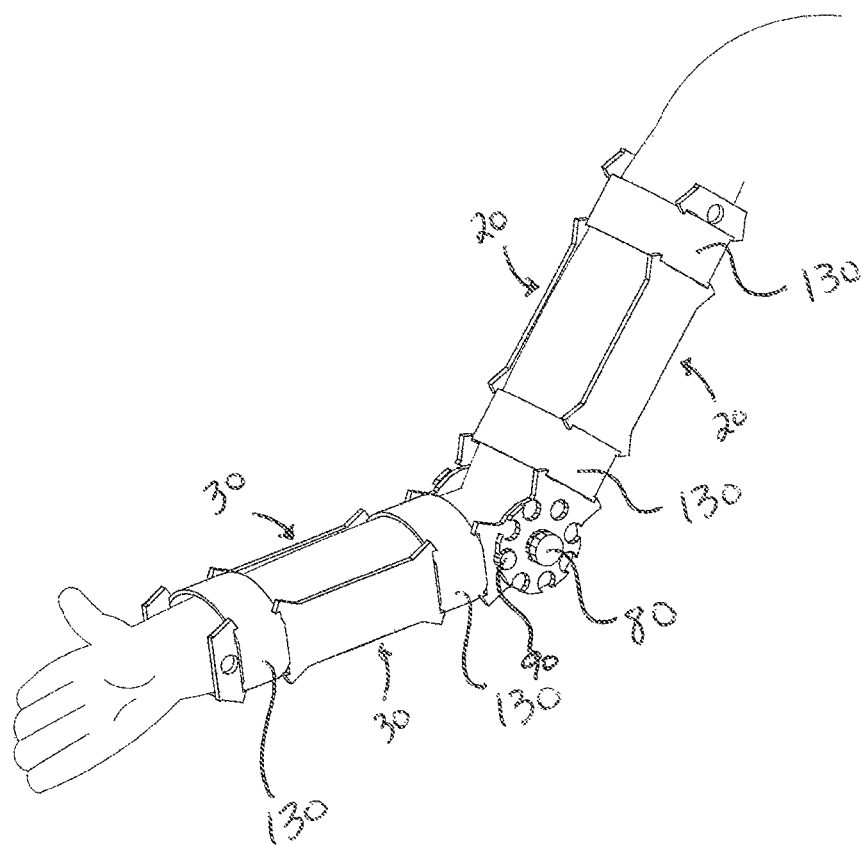
FIG. 10 illustrates a perspective view of the splint as applied to an arm according to various embodiments herein.
Figure 11:
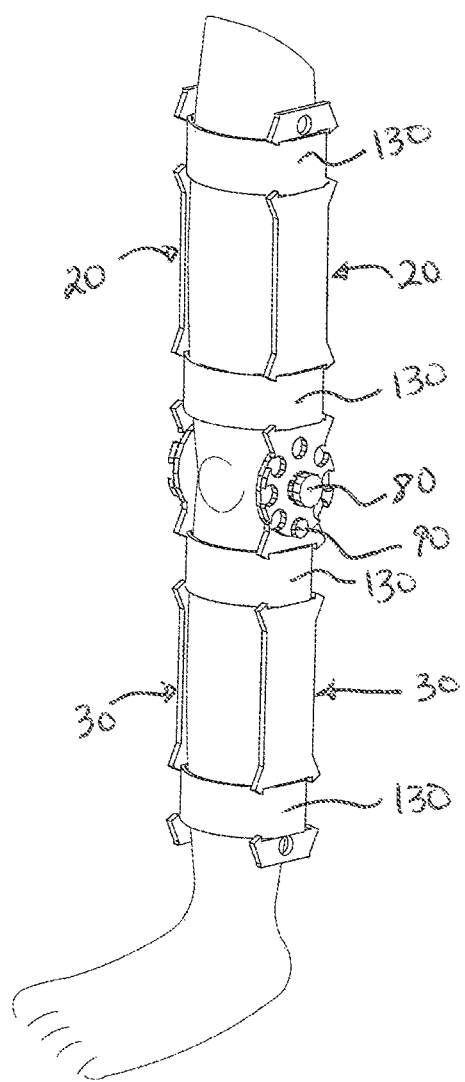
FIG. 11 illustrates a perspective view of the splint as applied to a leg according to various embodiments herein.

In another embodiment, the exterior surface of the male splint member 20 and female splint member 30 may be lined with a slip resistant material to assist in securing the members 20, 30 together when in a stacked relationship, or to a bodily limb when being used as a splint (as shown in FIGS. 10 and 11).

Figure 2:
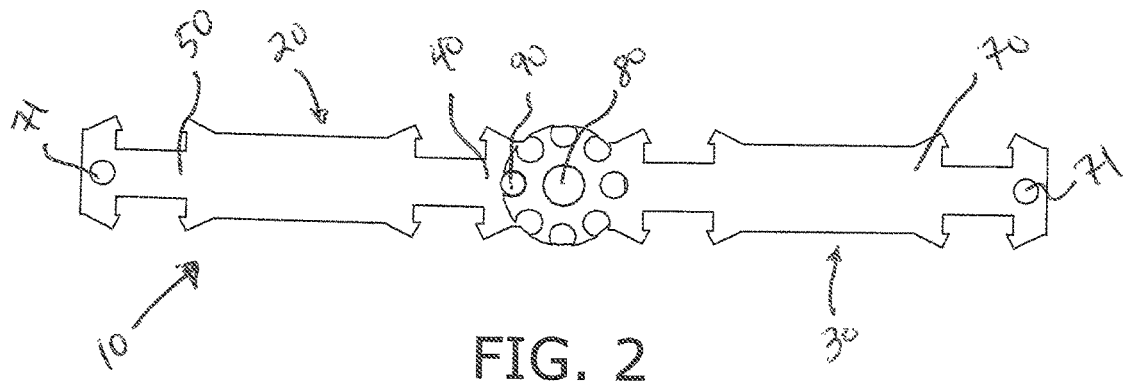
FIG. 2 depicts a top-down view of the splint halves joined in a 180° configuration according to various embodiments herein.
Figure 3:
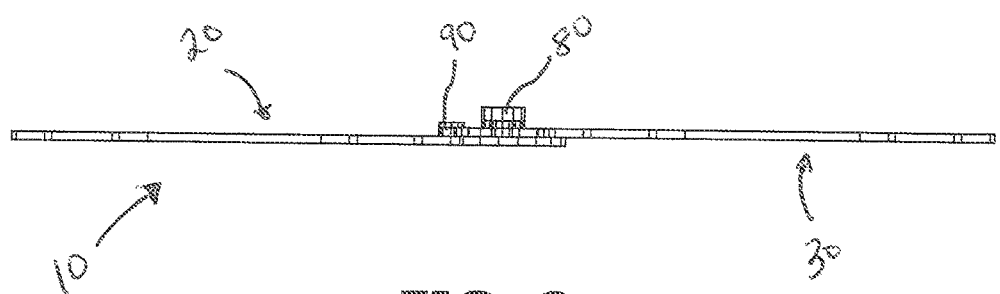
FIG. 3 depicts a side profile view of the splint halves joined in a 180° configuration according to various embodiments herein.
Figure 4:
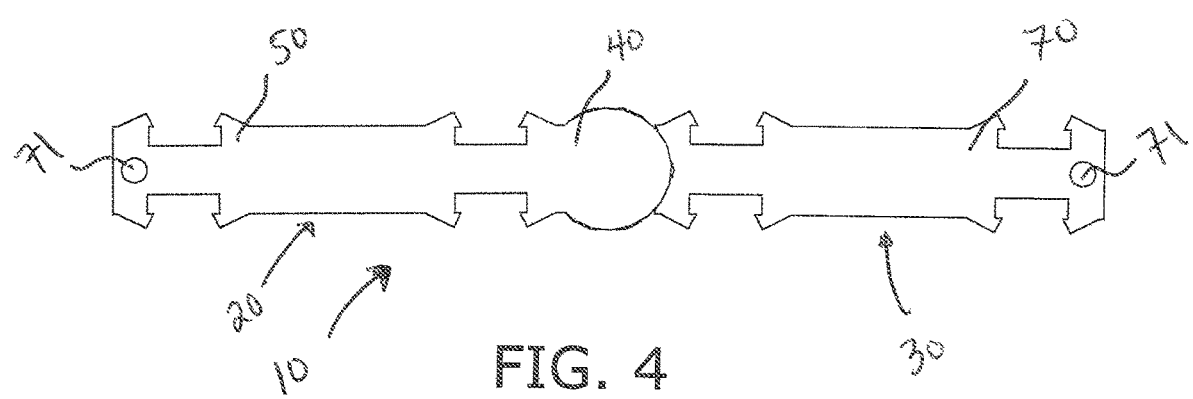
FIG. 4 depicts bottom-up view of the splint halves' contact side joined in a 180° configuration according to various embodiments herein.
Figure 5:
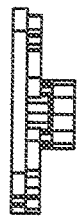
FIG. 5 depicts an axial view of the splint halves joined in a 180° configuration according to various embodiments herein.
Figure 6:
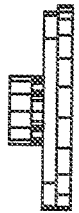
FIG. 6 depicts an alternative axial view of the splint halves joined in a 180° configuration according to various embodiments herein.
Figure 7:
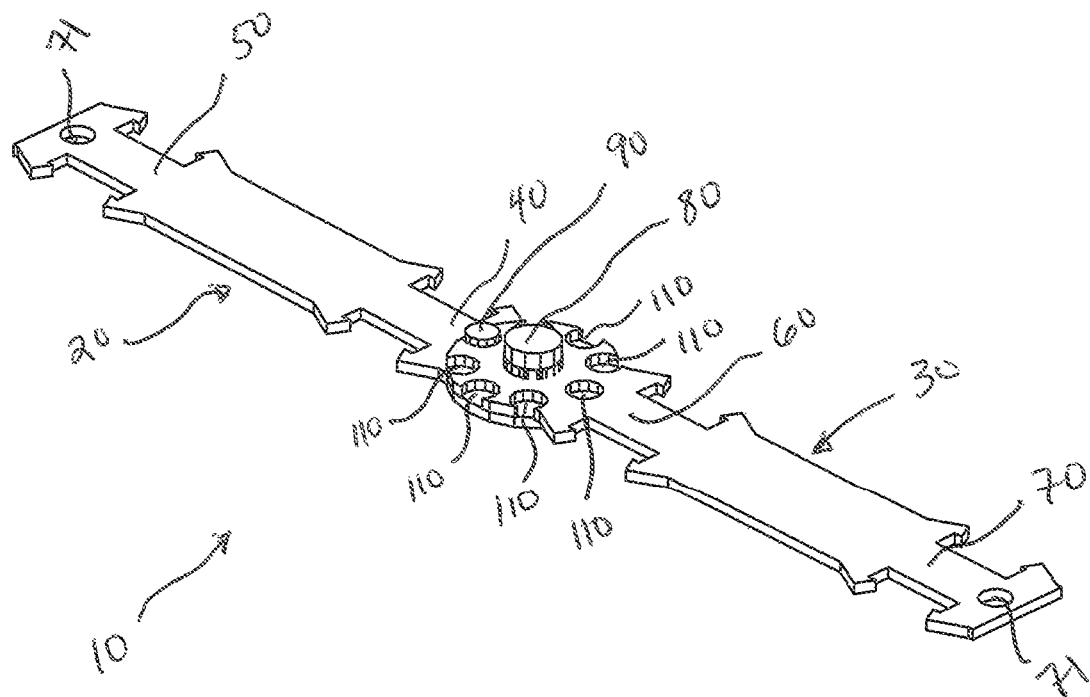
FIG. 7 depicts a perspective view of the splint halves interlocked in a 180° configuration according to various embodiments herein.

As shown in FIG. 2, a top-view of the splint 10 is shown with the male splint member 20 and female splint member 30 joined in a 180° configuration. In preferred embodiments, the user can secure such a configuration, on one or more sides of an injury, to provide joint immobility using strapping or other means. FIGS. 3-7 depict alternative views of the same configuration.

Turning to FIG. 10, a perspective view of the splint 10 is shown being used with an arm. In this embodiment, the splint 10 includes two male splint members 20 and two female splint members 30 positioned laterally and medially to the arm with the interlocking male and female splint members 20, 30 connected adjacent to the elbow joint. Binding straps 130 slotted through the strap receiving slots 120 on the splint members 20, 30 are used to secure the splint members 20, 30 to the bodily limb.

FIG. 11 illustrates a perspective view of the splint 10 as applied to a leg according to various embodiments of the present invention. Two sets of male and female splint members 20, 30 are positioned laterally and medially to the leg with the first end 40 of the male splint member 20 interlocking the first end 60 of the female splint member 30 adjacent to the knee joint. The splint members are secured to the leg by binding straps 130 secured around the leg and through the strap receiving slots 120 disposed along a length of the male and female splint members 20,30. In the preferred embodiment, the strap receiving slots 120 disposed on each pair of male splint member 20 and each pair of female splint members 30 are in alignment when the members 20, 30 are interlocked and positioned around a bodily limb, as depicted in FIGS. 10 and 11, and secured by fastening means, including but not limited to, hook and loop fasteners (e.g. VELCRO), snap buttons, clasps, or buckles.

In the preferred embodiment, the binding strap 130 is removable from the male and female splint members 20, 30, which allows for easy replacement when the strap becomes worn. However, alternative embodiments may include a more durable strap that is fixed, attached, or woven into the male or female splint members 20, 30.

While preferred materials for elements have been described, the device is not limited by these materials. Wood, plastics, rubber, foam, metal alloys, aluminum, and other materials may comprise some or all of the elements of the splinting halves, stabilization devices and apparatuses in various embodiments of the present invention.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims. For the purposes of promoting an understanding of the principles of the invention, reference has been made to the preferred embodiments illustrated in the drawings, and specific language has been used to describe these embodiments. However, this specific language intends no limitation of the scope of the invention, and the invention should be construed to encompass all embodiments that would normally occur to one of ordinary skill in the art. The particular implementations shown and described herein are illustrative examples of the invention and are not intended to otherwise limit the scope of the invention in any way. For the sake of brevity, conventional aspects of the system (and components of the individual operating components of the system) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

What is claimed is:

1. A splint comprising:
   a. a first male splint member having an interior surface and an exterior surface, wherein said first male splint member comprises a first end and an opposite second end, said first end comprising a locking post and an adjustable locking post, wherein said locking post is attached to said interior surface and extends outwardly from said first end along a first axis and wherein said adjustable locking post is attached to said interior surface and extends outwardly from said first end along a second axis, wherein said first axis and said second axis are parallel;
   b. a first female splint member, wherein said first female splint member comprises a first end and an opposite second end, said first end of said first female splint member comprising a locking aperture operable to receive said locking post along said first axis and a plurality of adjustable apertures, each of said adjustable apertures is operable to receive said adjustable locking post along said second axis;
      wherein said first male splint member and said first female member are configured to be in a fixed selected position,
      wherein said fixed selected position is exclusively determined by said locking aperture receiving said locking post along said first axis and selected one of said adjustable apertures receiving said adjustable locking post along said second axis, and
      wherein an alignment of said first male splint member and said first female splint member is configured to be angularly adjustable by adjusting which of the adjustable apertures is the selected adjustable aperture.

2. The splint of claim 1 wherein said plurality of adjustable apertures are disposed circumferentially along a perimeter of the first end of said first female splint member.

3. The splint of claim 2 wherein the alignment of said first male splint member and said first female splint member is angularly adjusted between 0 to 360°.

4. The splint of claim 1 wherein the first end and second end of said first male splint member and said first female splint member are configured to be secured together in combination around a limb by strapping means.

5. The splint of claim 1 wherein each of the first end and second end of said first male splint member and said first female splint member further comprise a strap receiving slot.

6. The splint of claim 1 wherein said first male splint members and female splint members is made from a material selected from the group consisting of thermoplastics or metals.

7. The splint of claim 1 further comprising a second male splint member and a second female splint member, wherein each of said first male splint member and said second male splint member is operable to be secured around a bodily limb, and wherein said first female splint member is operable to be secured around a bodily limb to said second female splint member, such that when secured, the splint is configured to secure a limb in a fixed position.

8. The splint of claim 7 comprising a means for attaching said first male splint member to said second male splint member.

9. The splint of claim 7 comprising a means for attaching said first female splint member to said second female splint member.

10. The splint of claim 1 comprising a mounting aperture at each of the second end of said first male splint member and the second end of said first female splint members.

11. The splint of claim 10 wherein the mounting apertures of said first male splint member and said first female splint member are aligned when said first male splint member and said first female splint member are configured in a stacked relationship.

12. The splint of claim 1 wherein an exterior surface of the first male and first female splint member comprises a slip resistant lining.

13. A splint used for holding a bodily limb in a fixed position, said splint comprising:
   a. at least two male splint members each having an interior surface and an exterior surface, wherein each said male splint member comprises a first end and an opposite second end, said first end comprising a locking post and an adjustable locking post, said first end and said second end of each of said male splint members comprises a strap receiving slot, wherein said locking post is attached to said interior surface and extends outwardly from said first end along a first axis and wherein said adjustable locking post is attached to said interior surface and extends outwardly from said first end along a second axis, wherein said first axis and said second axis are parallel;
   b. at least two female splint members, wherein each said female splint member comprises a first end and an opposite second end, said first end of said female splint members comprising a locking aperture operable to receive said locking post along said first axis and a plurality of adjustable apertures, each of said adjustable apertures is operable to receive said adjustable locking post along said second axis, said first end and said second end of each of said female splint members comprises a strap receiving slot;
   c. a plurality of binding straps, wherein each of said plurality of binding straps is sized and dimensioned to fit within each of said strap receiving slots of said male and female splint members;
      wherein said male splint members and said female splint members are configured to be in a fixed selected position,
      wherein said fixed selected position is exclusively determined by said locking aperture receiving said locking post along said first axis and by receiving a selected one of said adjustable apertures receiving said adjustable locking post along said second axis, wherein an alignment of said male splint member and said female splint member is configured to be angularly adjustable by adjusting which of the adjustable apertures is the selected adjustable aperture, wherein said plurality of binding straps are operable to secure each said male splint member to the other male splint member around a bodily limb, and wherein said plurality of binding straps are operable to secure each said female splint member to the other female splint member around a bodily limb, such that when secured, the splint is configured to secure the bodily limb in a fixed position.

14. The splint of claim 13 wherein said plurality of adjustable apertures are disposed circumferentially along a perimeter of the first end of said female splint member.

15. The splint of claim 14 wherein alignment of said male splint member and said female splint member is angularly adjusted between 0 to 360°.

16. The splint of claim 13 wherein each of said male splint members and female splint members is made from a material selected from the group consisting of thermoplastics or metals.

17. The splint of claim 13 comprising a mounting aperture at the second end of each said male splint members and the second end of each said female splint members.

18. The splint of claim 17 wherein the mounting apertures of said male splint member and said female splint member are aligned when said male splint members and said female splint members are configured in a stacked relationship.

19. The splint of claim 13 wherein an exterior surface of the male and female splint members comprises a slip resistant lining.

* * * * *